(12) United States Patent
Chang

(10) Patent No.: US 6,536,058 B1
(45) Date of Patent: Mar. 25, 2003

(54) PREFORMED SHAPE HEADREST

(76) Inventor: Pei-Yeh Chang, No. 1-4, Lane 71, Sec. 1, Hang Chou S. Rd., Taipei (TW)

( * ) Notice: Subject to any disclaimer, the term of this patent is extended or adjusted under 35 U.S.C. 154(b) by 0 days.

(21) Appl. No.: 09/714,394

(22) Filed: Nov. 16, 2000

(30) Foreign Application Priority Data

Oct. 24, 2000 (TW) .......................... 89122381 A (51) Int. Cl.⁷ .................................. A47G 9/10
(52) U.S. Cl. ................. 5/636; 5/637; 5/640; 5/643; 5/655
(58) Field of Search .................. 5/636, 637, 640, 5/643, 644, 645, 655

(56) References Cited

U.S. PATENT DOCUMENTS

| | | | | |
|---|---|---|---|---|
| 2,940,088 A | * | 6/1960 | Boos | 5/636 |
| 4,825,487 A | * | 5/1989 | Eberl | 5/636 |
| 5,127,120 A | * | 7/1992 | Mason | 5/637 |
| 5,781,947 A | * | 7/1998 | Sramek | 5/640 |
| 6,052,850 A | * | 4/2000 | Salido et al. | 5/637 |
| 6,263,526 B1 | * | 7/2001 | Tu | 5/655 |
| 6,266,832 B1 | * | 7/2001 | Ezell | 5/636 |

* cited by examiner

*Primary Examiner*—Michael F. Trettel
(74) *Attorney, Agent, or Firm*—Knobbe, Martens, Olson & Bear, LLP (57) ABSTRACT

A headrest device for holding the neck and head of infants to assist the development of the shape of their skull. The device includes a base, the outside contour of which is concave for holding the head and designed according to the measurement of the average of different head shapes of normal newborn babies. A depressed segment of the base is used to support the infant's typically weak neck. A removable supplement and a direct-contact piece are included as well in this headrest device.

13 Claims, 14 Drawing Sheets

Asymmetric index distribution table in normal babies' skull

| Age | No. of case(%) in four AI intervals | | | | Total no. of cases | Avg. AI |
|---|---|---|---|---|---|---|
| | <30 | 30~60 | 60~90 | >90 | | |
| 4d | 33(31%) | 67(64%) | 5(5%) | – | 105 | 37.3 |
| 1m | 53(47%) | 46(41%) | 13(12%) | – | 112 | 36.5 |
| 2m | 34(35%) | 40(41%) | 15(15%) | 9(9%) | 98 | 46.2 |
| 3m | 57(41%) | 59(42%) | 16(11%) | 8(6%) | 140 | 41.9 |
| 4m | 55(48%) | 39(35%) | 14(13%) | 4(4%) | 112 | 40.0 |
| 5m | 55(44%) | 44(36%) | 19(15%) | 6(5%) | 124 | 40.4 |
| 6m | 58(54%) | 35(32%) | 12(11%) | 3(3%) | 108 | 36.3 |
| 9m | 65(60%) | 36(34%) | 3(3%) | 3(3%) | 107 | 33.4 |
| 1y | 74(51%) | 57(39%) | 9(6%) | 5(4%) | 105 | 36.0 |
| 7y | 24(41%) | 31(54%) | 3(5%) | – | 58 | 34.5 |
| 9y | 30(60%) | 19(38%) | 1(2%) | – | 50 | 39.4 |
| 12y | 28(53%) | 21(40%) | 4(7%) | – | 53 | 31.5 |

(normal babies)

PREFORMED SHAPE HEADREST

RELATED APPLICATIONS

This application claims the benefit of the Taiwanese application 89122381 filed Oct. 24, 2000.

BACKGROUND OF THE INVENTION

1. Field of the Invention

The invention relates to a non-compressed, preformed shape headrest, particularly useful for shaping infants' heads during skull formation. The headrest is adapted to be adjustable in size as the head grows.

2. Description of the Related Art

Figure 1A:
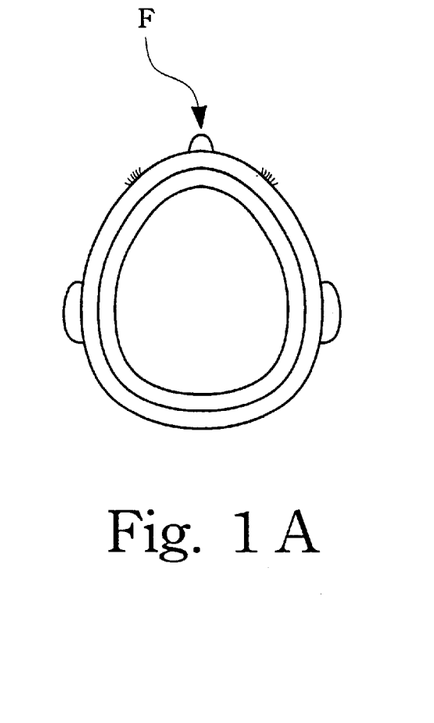
FIG. 1A to FIG. 1D are vertical views of infant skull shape, showing a variety of sleeping positions of newborn babies with respect to the change of their skull shape.
Figure 1B:
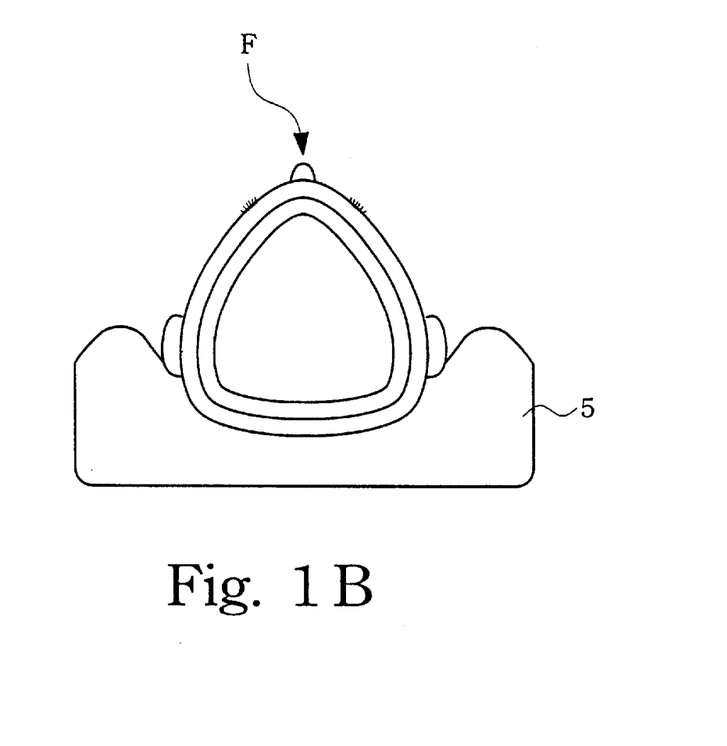
Figure 1C:
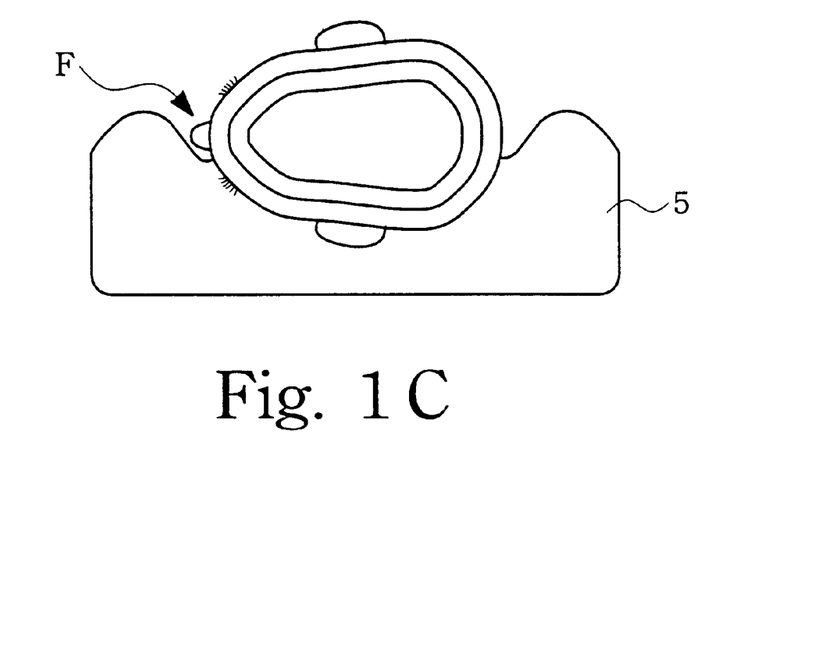
Figure 1D:
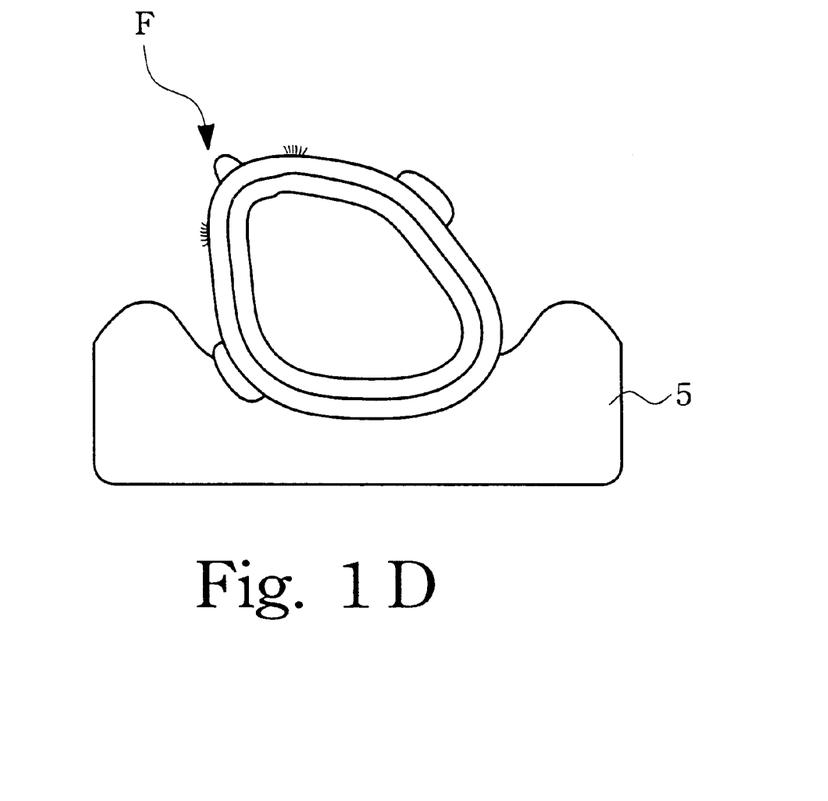

Oriental newborn babies usually sleep lying face up. As a result, in the process of skull formation, they tend to suffer more flat head on the back of the skull than babies from the West who usually assume a prone sleeping position. FIG. 1A and FIG. 1B show different sleeping positions with a vertical view. F shows the face on the front side of the baby who sleeps on the pillow 5. FIG. 1A shows a normal skull shape of a newborn baby while FIG. 1B illustrates the head shape of a baby sleeping on his back. FIG. 1C shows the head shape of baby lying on the side or tummy while FIG. 1D illustrates a side effect of assuming a single-sided sleeping position, namely an asymmetric skull shape.

Generally, the skull of a baby in the mother's body is rather supple in order to pass through the birth canal. After the baby is born, his skull forms more solidly for the brain's protection. The formation of the infant's skull shape is largely determined in the first couple of months after birth. This means that adjustment of skull shape is preferably taken shortly after the baby is born. The inventor mentions the development of face shape of a torticollis infant after a long-term investigation in his published "Torticollis: a long term follow up study" at *Acta Paed Sin. volume* 37(3), P.173–177 in 1996. The findings of this study show that the skull shape formation occurs substantially in the couple of months immediately following the baby's birth. Therefore, skull deformity can be largely avoided if preventions are taken early during the period of skull formation. The situation of a premature infant is typically even worse. Some past studies have made use of a water pillow to release the point pressure from weight on skull formation without substantive effect.

Currently, in the street stalls, the principle for the infant-specific pillow is the same as that for adults, i.e. a pillow made of cotton material, polymer, or synthetic fiber with a cloth covered outside. Unfortunately, the infant head still suffers from the weight of around 0.5 kg to 1 kg under the structure, making his head flat, and pillows of this kind cannot adequately relieve the point pressure from the baby's head weight. Furthermore, some pillows are produced in a donut-like shape, in which only a piece of cloth is stuffed inside an outer soft-and-tender cover. These have been proven to not work well at all in the period of skull formation.

Figure 2:
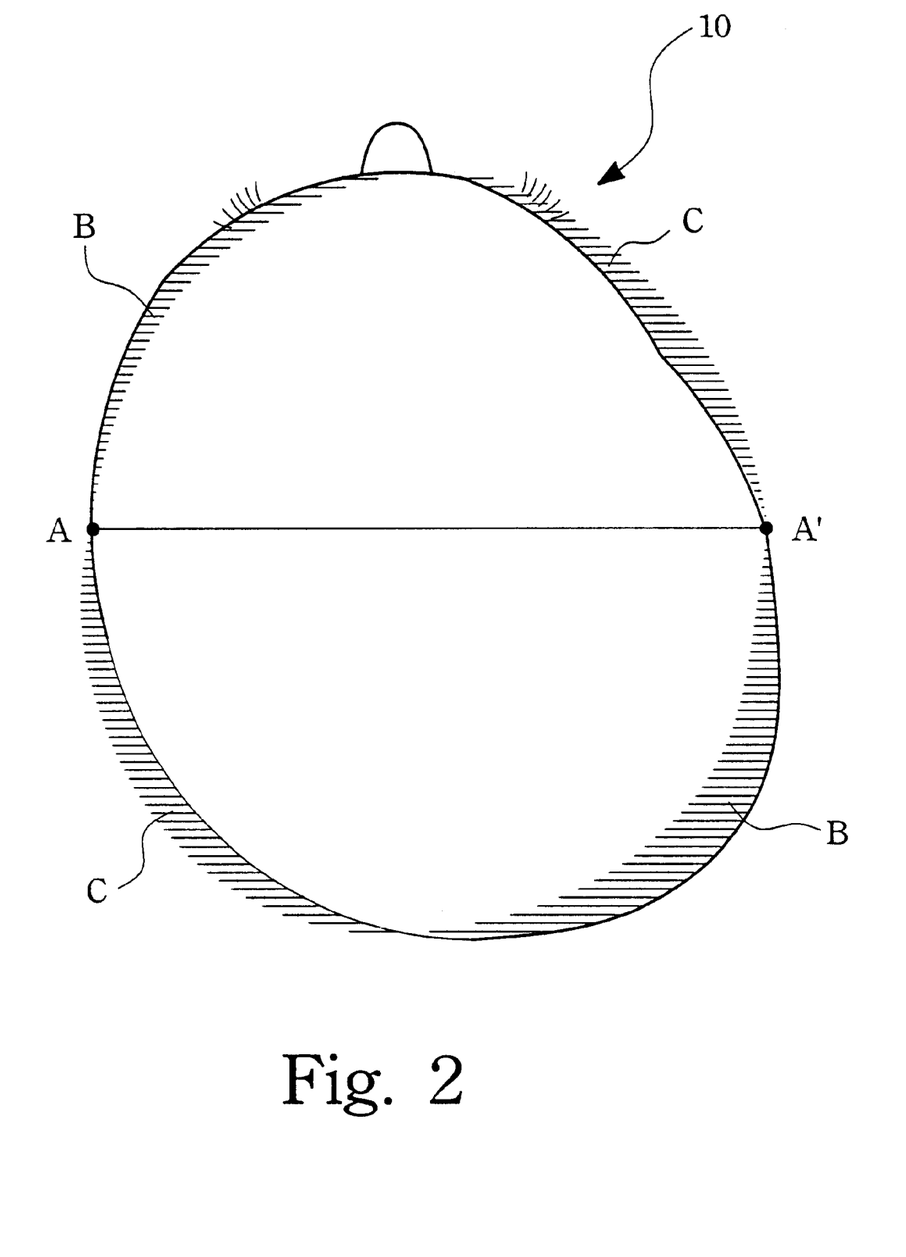
FIG. 2 is a vertical view of infant skull shape, proving that the change of skull shape influences the development of face shape.

The previously mentioned, investigation has revealed that in the 4 months before and after the baby is born, the head of the baby can become deformed gradually due to bad sleeping positions. It is also suggested that 4.8% of the infants have abnormal skull shapes when they are born and 16–23% of infant skull shapes show asymmetric changes after 2–4 months. Especially with the increase of their age, the skull forms more solidly and the change becomes more fixed and it will not have any apparent change persisting into adulthood. Of interest is that the change of skull shape is always coincident with the development of facial appearance. Please refer to FIG. 2, which provides a vertical view of an infant skull; the arc line 10 represents the vertical view of a deformed skull; point A and A' show the position of the left and right ears, separately; the upper part of arcs of point A and A' show the face shape; the oblique line B shows the bulge area of the face as differs from a normal, symmetric one; the oblique line C shows the indented face a compared to that of the normal with symmetry. These prove that a change of skull shape is quite relevant to the face development. Once an asymmetry is formed, it becomes difficult to adjust afterwards. Therefore, keeping a symmetric and round skull shape contributes greatly to the beauty of outside, facial appearance in the future.

Figure 3A:
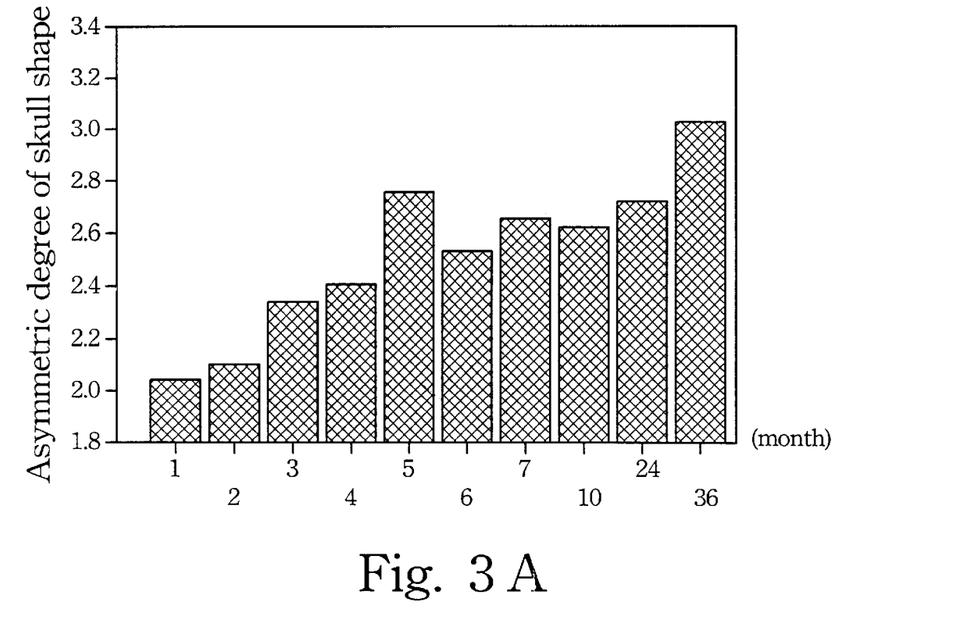
FIG. 3A illustrates the result of measurement of infant skull deformity, showing the degree of skull tilt becomes more serious with infant growth.
Figure 3B:
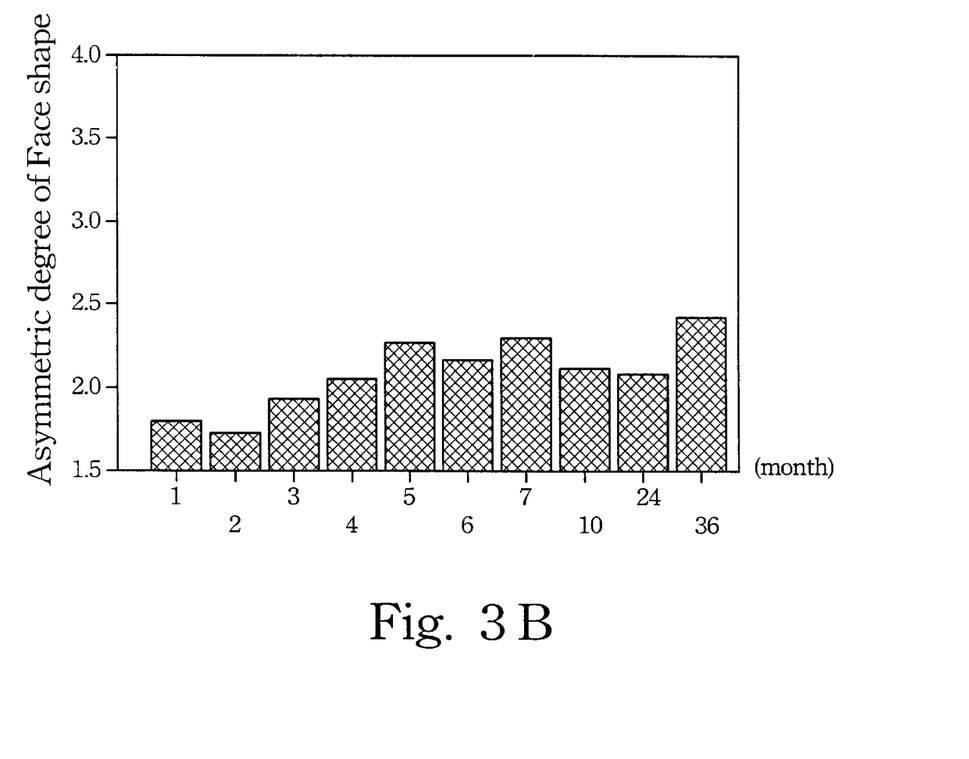
FIG. 3B shows the results of measuring the facial shape of a baby with abnormal skull shape, showing the change of infant skull leading to the change of face shape.

FIG. 3A illustrates the result of deformed skull measurement. Axis Y shows the degree of mean assessed skull asymmetry, wherein the definition of the asymmetric degree—level 1 to 4—stands for the normal, the slightly deformed, the moderately deformed, and the seriously deformed respectively. From the Figures, one can observe that with the growth of the infant, the deformity degree of his skull shape can become more and more asymmetric. FIG. 3B illustrates the result of deformed skull measurement, revealing the influence of skull changes on facial development, among which the degree of the influence becomes greater than the slightly deformed after 3 months.

Figure 4:
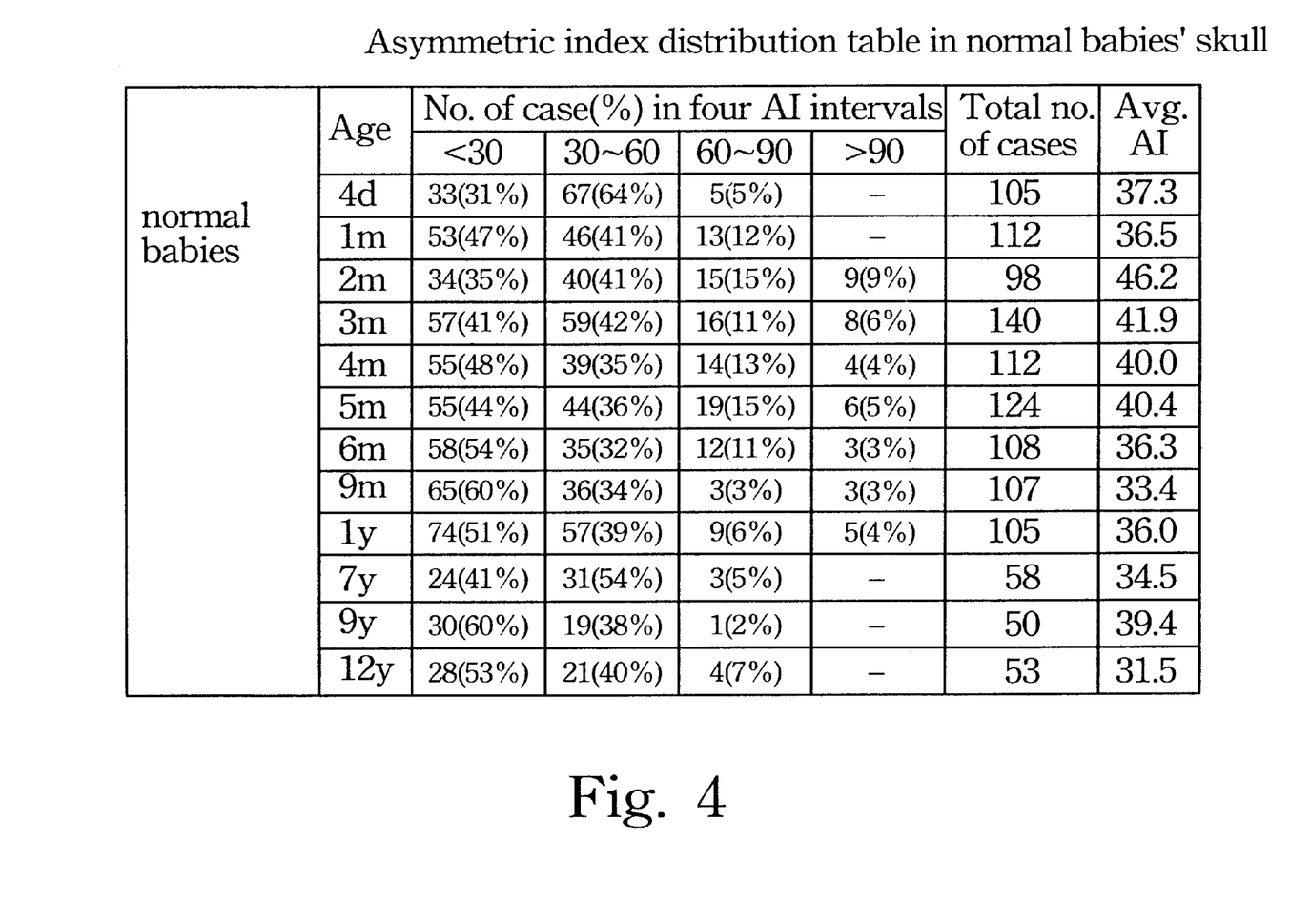
FIG. 4 shows the average of severity of skull deformity of normal infants, using malleable splint material and plastic mould to record, showing that even a normal baby has the tendency of skull deformity.

FIG. 4 reflects the severity index average of normal babies by plaster mould records, in which 0–30 means normal, 30–60 the slightly deformed, 60–90 the moderately deformed, and 90 and above mean seriously deformed. It proves that even a normal infant can experience the phenomenon of deformity. The inventor's study shows that the percentage of babies developing asymmetric skulls is about 10% in otherwise normal skull babies. It is believed that, because the sleeping position of most Oriental babies is lying face up, the contacting pressure is not focused on the center of head, and tiny deviations will cause the asymmetry of skull development.

The flat shape does not apparently influence the development of intelligence but does influence the eventual shape of the face. As far as the inventor can see, a headrest device able to relieve such a problem is still not available in commercial markets. Furthermore, if a baby has torticollis, then it is required to provide a device to prevent the deformity. It becomes an essential issue to design a pillow based on the principle of human engineering, by which the head of both premature and newborn babies could acquire a relief from excessive point pressure.

SUMMARY OF THE INVENTION

The purpose of this invention is to provide a non-compressed headrest to aid skull formation of newborn babies and those under 1 year old, by which the outside appearance of their face and head is maintained, as the skull deformity can be adjusted.

This invention is also about a device used to hold the head and neck of a baby in order to maintain the original skull shape while he is sleeping with his face up. The device includes a base, the shape of which is concave for holding the head and designed accordingly by the measurement of the average of different baby head shape of normal newborn babies. Moreover, a depressed segment below the base is used to support the infant's neck. This device can be used to adjust the abnormal skull shapes caused by torticollis or other reasons. Additionally, the concave base and the depressed segment are flexible and won't bend or deform during holding the baby's head. The Shore A hardness of the device is in between 0 to 40, and the device can be made of materials including silicon, polyurethane, plant fiber, artificial fats, polyethylene, polystyrene, polymer, foamed rubber, and plastics and so on. The compression ratio while holding baby head and neck is preferably <25%. The compression ratio is calculated by (M−N)/M, where M is the height of the device and N is the height when the device is in use.

In another practical instance, the base for the head of premature infants includes a concave area with a descending circumference around it, which is used for holding the baby's neck and shoulder. The base not only provides premature infants with soft-and-tender support for the formation of ideal skull shape, but also helps breathing. As a result, by using the device, the formation of the ideal skull shape and a better breathing position can be achieved.

The improvement of this head holder includes three major parts including a base, a supplement, and a direct contact piece, among which the base is manufactured according to the ideal skull shape and the size can be larger than the actual size of the user's head. As for the supplement, it is designed as a smaller non-compressed sheet, covering the base, on which the smaller size of newborn baby can use as well. Moreover, it can continue to be used, even after the baby grows, by only changing or removing the supplement.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

As previously discussed, the skeleton of both premature and newborn babies remains not fully calcified and thus the formability thereof is unpredictable, but during the 6th month to 2 years old, the skull becomes fixed and hard. In other words, the skull shape won't be easily changed after 2 years old and many phenomena have shown and proven it. During the period of skull shape formation, different kinds of resultant skull shapes can be observed if we let the baby sleep in different positions. For instance, the cephalic index (CI) of the infant generally sleeping with their face up is larger than of those generally sleeping face down. Generally, Chinese infants sleep face up and the value of CI is 100. This phenomenon is not due to different races since the value decreases down to 80–85 after taking the sleeping position on abdomen or on the side.

The skull shape of premature babies is relatively long and the cause of dolichocephaly is that: firstly, the baby is given birth earlier and thus plasticity of the skull is greater; secondly, the child lacks the strength in the neck to support or move the weight of his head and thus typically sleeps on the side and uses an incubator to aid his growth. Sleeping on the side helps the use of respirators and inhibits vomiting. As a result, long-term sleeping on the side often leads to the shape of dolichocephly.

The prebirth skull shape of newborn babies reveals roundness. It is because they grow up in a womb filled with water, within which the baby grows without specific pressure. Once the baby is born, his neck is generally not capable to hold his head until the $6^{th}$ week. After birth, the skull shape changes gradually by influence of Earth gravity and only a small or even a spot of area of the round head supports the weight of head. Accordingly, if there is any deviation away from a six o'clock orientation, the middle most, the tendency towards skull deformity occurs. FIG. 4 shows the percentage of asymmetric skull shape (calculated as an asymmetric index more than 60) is more than 10%. Sleeping on the side or lying on the abdomen causes less deformity. Owing to the supporting strength coming from left and right temporal areas, the occipital area is round but the overall skull shape tends towards an oval. To those lying with their face up, the pressure of weight from the back can lead to brachycephaly.

In order to prevent newborn babies sleeping face up from any resulting problem, such as brachycephaly, torticollis, and dolicoccephaly such as may occur with premature babies and those babies who sleep on their abdomens, it is sometimes necessary to use a preformed shape pillow to maintain the shape of skull. The implementation of the use of this pillow is firstly to measure a set of skulls of newborn babies with different size and shapes, then to calculate the average value i.e. the ideal of the skull shape, and to design the ideal skull shape into a head holding headrest.

It can be found by using pressure sensors for measuring the effect in the use of different pillows during infant sleep that: (1) the pressure is the highest (140 mmHg) without any headrest; (2) the pressure sensor indicates 80 mmHg (which remains high) with the flat headrest made of sponge or foamed materials; (3) the preformed shape pillow is able to reduce pressure down to only 26 mmHg; (4) continental-quilt- or cotton-made headrest (adult's pillow with at least 10 cm height) reduce the pressure to 45 mmHg.

In all, the preformed shape pillow and cotton-made soft pillow is to reduce the pressure by enlarging direct-contact area against the baby's head. The simple pillows or headrests mentioned above cannot (1) fix sleeping position and (2) form the ideal shape of skull. In other words, though cotton-made pillow can relieve pressure, it requires a height of 10 cm and still can't guarantee to avoid brachycephaly and dolicocephaly but merely lessen the pressure effect.

Therefore, the non-compressed preformed headrest for newborn and premature babies of this invention can effectively prevent skull deformity and achieve the ideal shape of skull formation. The headrest for the premature baby refers to the mattress or a supplement in incubator, which should be designed in a preformed shape, the principle of which is noncompressed and of ideal skull shape for producing the headrest device with fixed shape.

This invention provides the device of a non-compressed preformed shape pillow for the protection of the developing skull shape of newborn and premature babies as well as their facial beauty and attractive shape of their head. Besides, the non-compressed preformed shape headrest is a supporter of the baby's head and neck to resolve the problem of weakness of the neck to hold the weight of their head. Furthermore, this device can also be used for adjust torticollis and skull shape changes from other reasons.

Figure 5A:
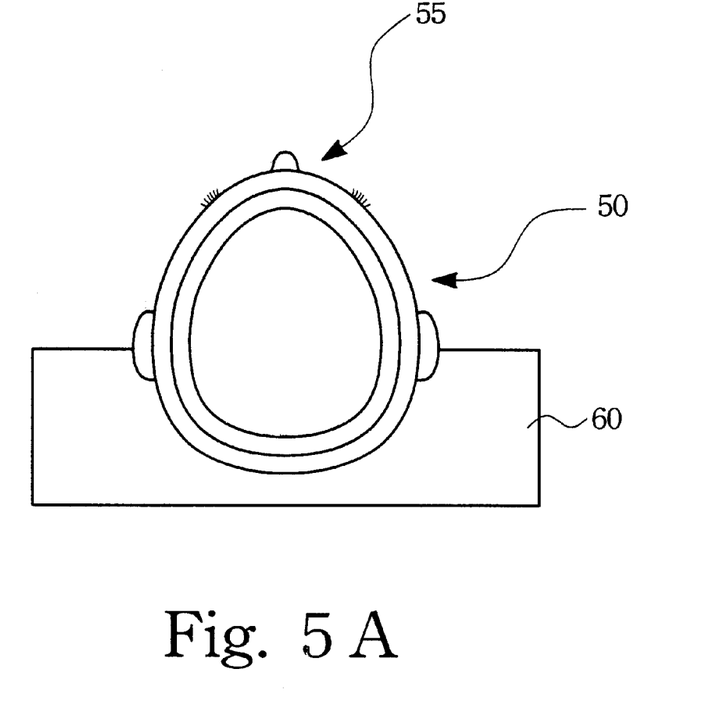
FIG. 5A is a top view of a skull module, showing the formation of the skull shape by using the impression powder of odontology in daily surgery according to this invention.
Figure 5B:
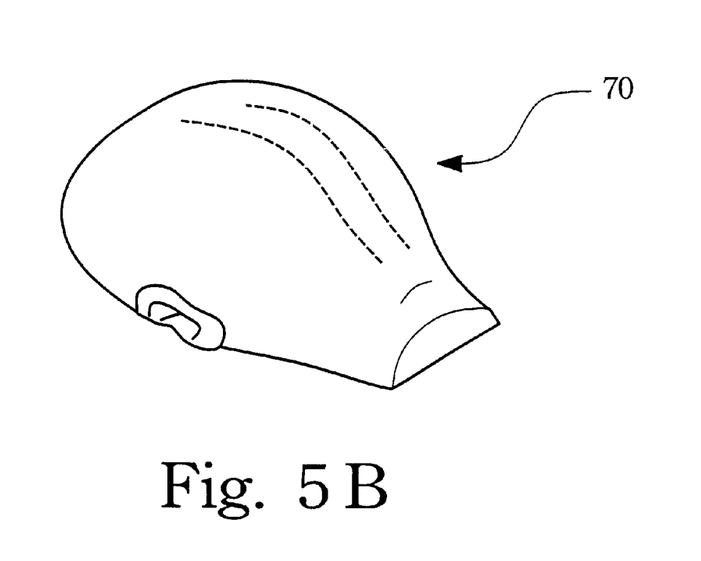
FIG. 5B illustrates a mould of normal baby skull, showing the formation of the original skull shape by application of this invention.

Firstly, please refer to FIG. 5A. By using impression powder, such as of odontology, a mould is made of the head 50 of an infant with normal skull who takes herniotomy or other small operations like the kind. In the process, the baby head 50 lies with face up on the impression powder 60 with the baby's face 55 upward and plaster is put into the concave shape formed by the impression powder 60, by which the mould 70 of original skull shape shown in FIG. 5B is obtained. According to the steps above, the skull mould 70 can be distinguished via the age and weight of babies in order for achievement of skull shape with more accurate correspondence to the age of each growth period.

Figure 6:
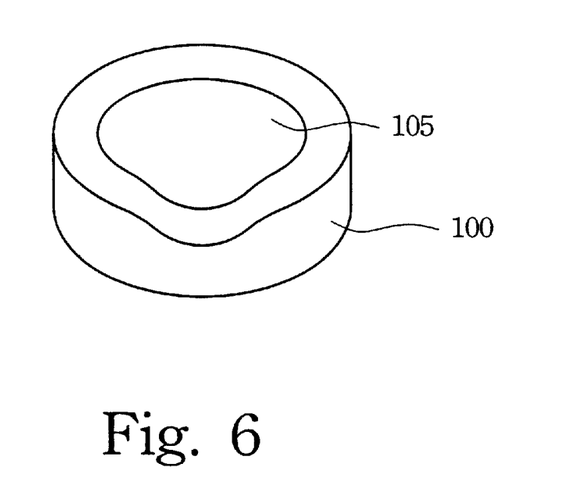
FIG. 6 illustrates a mould of an ideal skull of a normal infant with respect to the mould of the pillow, showing the formation of an ideal skull shape and manufacture of the pillow according to this invention.
Figure 7:
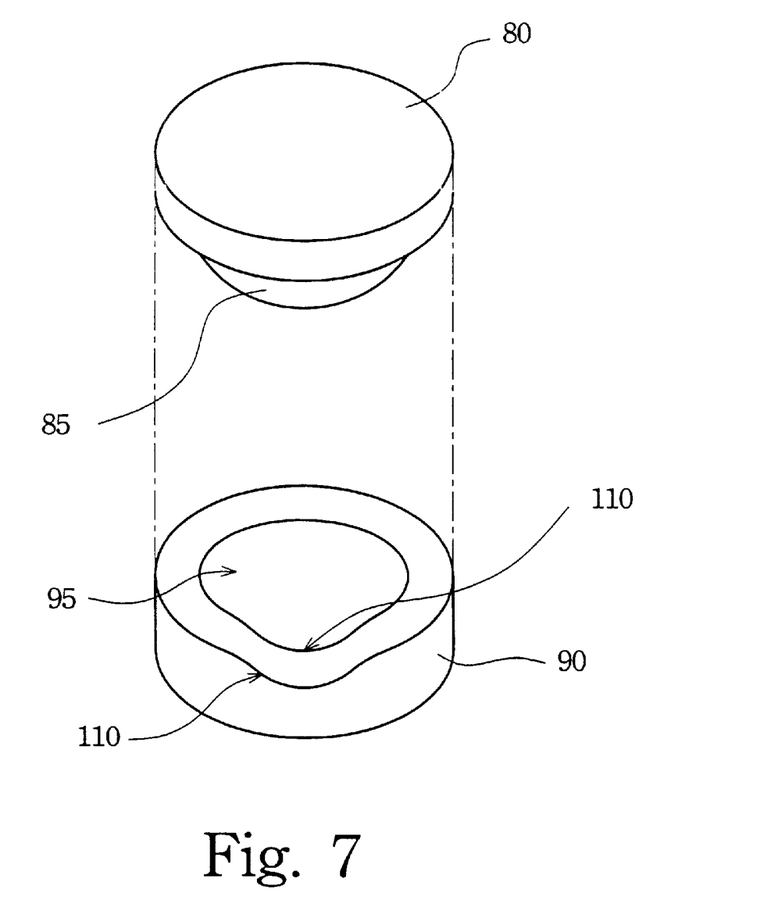
FIG. 7 illustrates a mould of the pillow showing the necessity of circumference for holding head and neck in order for producing the according mould of the pillow or the device as the head supporter for premature infants according to this invention.

Afterwards, record the 3-dimensional moulds and their relevant 3D data representation and make statistics for the ideal skull shape with different ages and weights, by which the mould of the pillow 100 in FIG. 6 is formed, among which is a concave area 105 for the ideal skull shape. According to records of the weight distribution from the baby's head and neck, design and modify the concave area, the depressed segment area, the width, the thickness and its shape, wherein the essentials parts are those holding the baby's head and neck. In accordance with the mould of pillow 100, the mould 80 shown in FIG. 7 is formed, among which the central bulge part 85 is the ideal skull shape calculated by statistics. Then, the mould of the pillow 90 is produced with respect to the mould 80; and the mould of pillow 90 shown in FIG. 7 includes the bulge part 85 in the middle of the skull mould 80 and its complement concave part 95 and the depressed segment area 110 used for holding the baby's neck. In practice, the mould 90 is made of silicon rubber.

Figure 12:
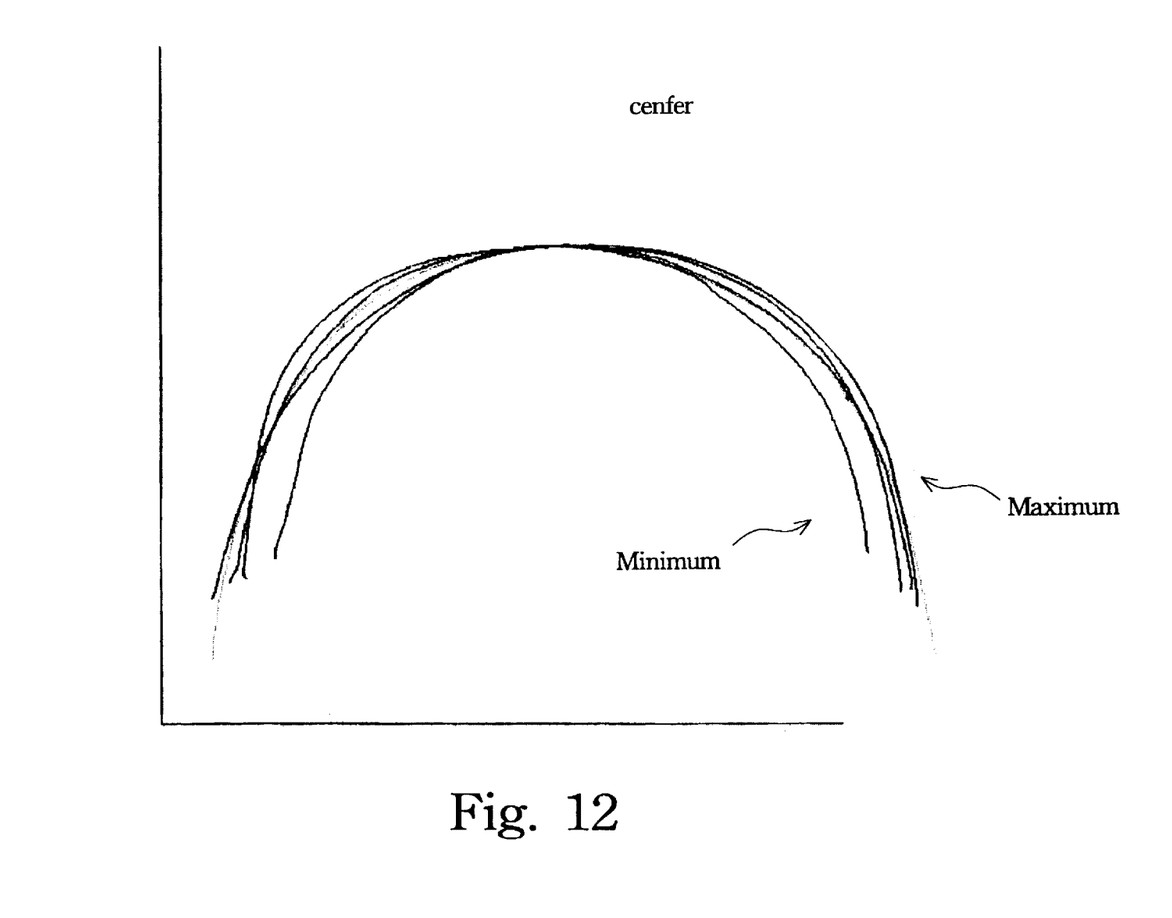
FIG. 12 is a diagram of the measurement of the position of parts of the skull for the babies in different ages with different weights, based on this measure, showing that the supplement can be designed so a smaller size can be achieved when the supplement is put into the base.
Figure 13:
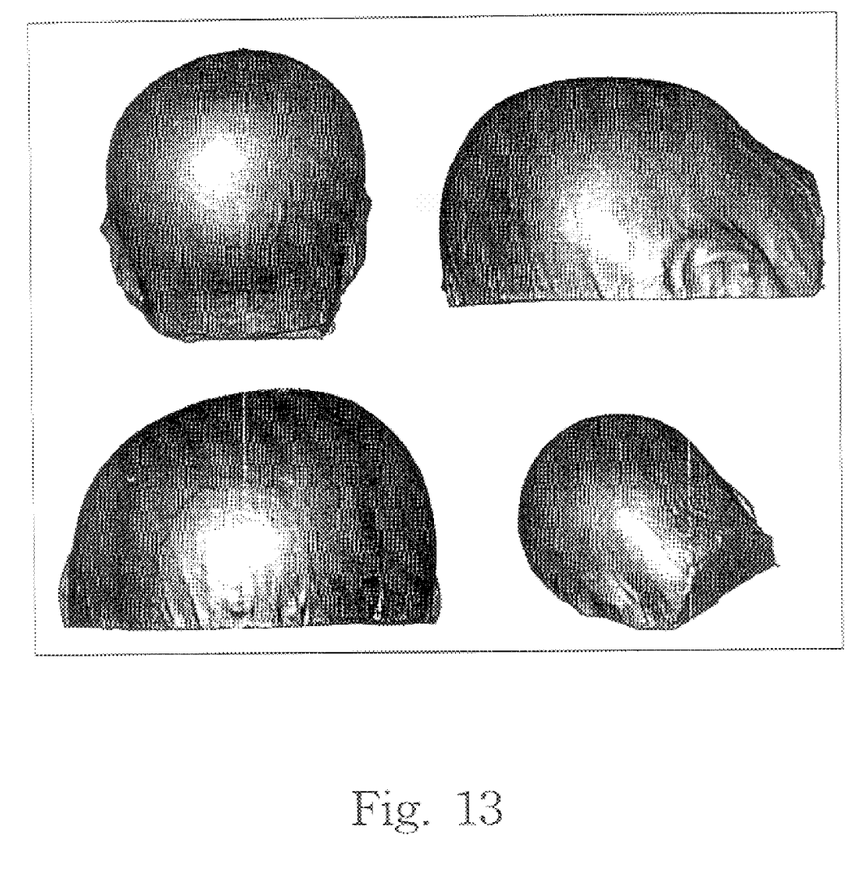
FIG. 13 illustrates a mould of a baby's skull.

In addition, the inventor as a pediatric surgeon has more opportunities to measure the skull models with respect to the babies with different ages and weights, shown in e.g. FIG. 12. FIG. 12 is a diagram of a method of measurement of the position of part of skull for the babies at different ages with different weights, and based on this measure, the supplement can be designed so that a smaller size can be achieved when the supplement is put into the base. Put these skull models on a 3D laser scanner and calculate the average and ideal size of the skull. Therefore, as FIG. 12 shows, the inventor is able to design a supplement of headrest for adapting to the different head shapes at different ages and weights.

Then, a pressure sensor piece is placed over the mould of pillow 90 for further testing of pressure distribution. By the pressure distributions measured, the mould 90 is modified until, in a complete fit of human engineering, the weight is evenly spread on the mould 90. Because the formation of the mould 90 of the pillow corresponds to the ideal skull shape, which may have slight differences, it enables the user to adjust in accordance with the sleeping position of the baby or with the actual situation of the baby (i.e. normal or abnormal with e.g. torticollis). At last, repeat the steps mentioned above to produce the final non-compressed preformed shape headrest, the major function of which is used for the baby to grow in the fixed mould of the pillow. To those so preformed, the long and narrow skull shape can be avoided.

The function of the headrest is to have the baby skull shape grow in accordance with the mould. The most important aspect is to keep the mould shape the same for the ideal skull shape when in use without deforming itself. In addition, the device must provide the baby's head with soft and tender support and be able to support the weight from 0.3 kg to 1.5 kg (depending on age and weight of head), which suggests a material with Shore A hardness in between 0 and 40 and compression ratio under 25% when holding baby head should be selected for the device. The configuration of the height of middle most region of the pillow without load is M and the height at the same position when the baby head on the pillow is N. The compression ratio is calculated by the formula $(M-N)/M$. In general, the material can be silicon, polyurethane, plant, artificial fats, polyethylene, polystyrene, PVC, ABS, gel, polymer, foamed rubber, and plastic materials and so on.

Since premature babies were given birth without complete growth, their skull is even softer than normal babies, and therefor demand more extensive support. In addition, a premature baby generally has many kinds of physiological problems so that use of a respirator and incubator are almost always indicated. It is shown that they need a smaller and softer headrest for holding their head, which is manufactured according to the average and ideal skull shape, calculated by several skull shapes of newborn babies. In addition, the solution to the use of small skull size is, adhere the supplement to the headrest mat in the device or make them as a unitized assembly. In order to account for the normal growth of skull shape, the supplement can then be removed and becomes one size larger.

Figure 8:
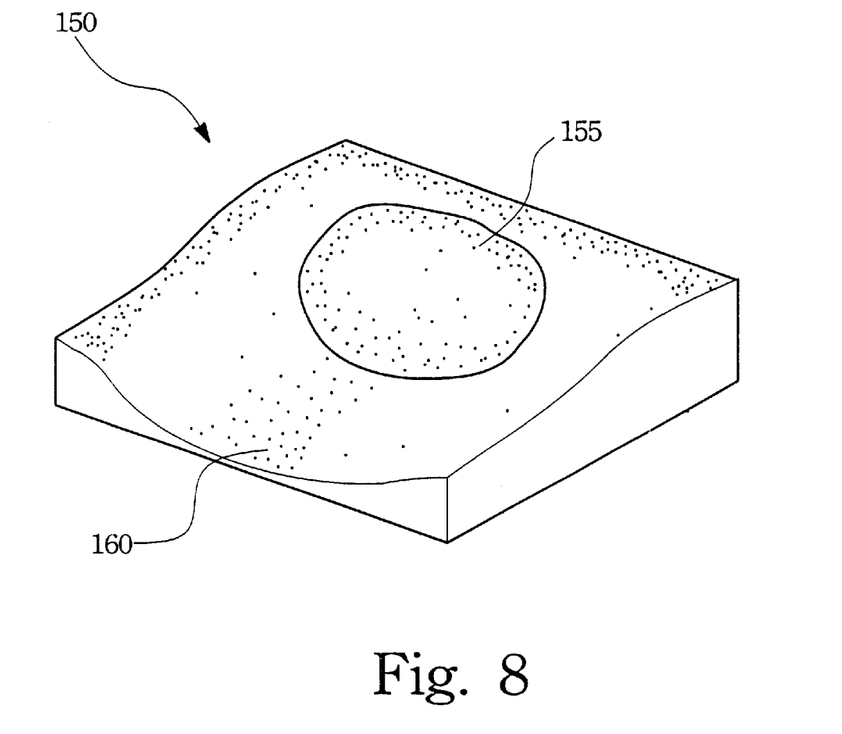
FIG. 8 shows a mould of the headrest for the premature infant, showing the mould of premature infant head, neck and shoulder according to this invention.

In a better practical instance, FIG. 8 shows the headrest 150 that the premature baby uses, including a concave area 155 for holding and protecting the baby's head, and a tilt circumference area 160 for holding his neck and shoulders. Other than holding the heads of premature babies with comfort and pressure distributed evenly so as to maintain their ideal skull shape, the headrest 150 helps smooth and ease the child's inspiration. Particularly for those under 1.5 kg when given birth, they need an inspirator for smoothing their breathing. By means of the supplement mentioned above, it smoothes the baby breathing and shapes the ideal skull of one size smaller babies.

Figure 9A:
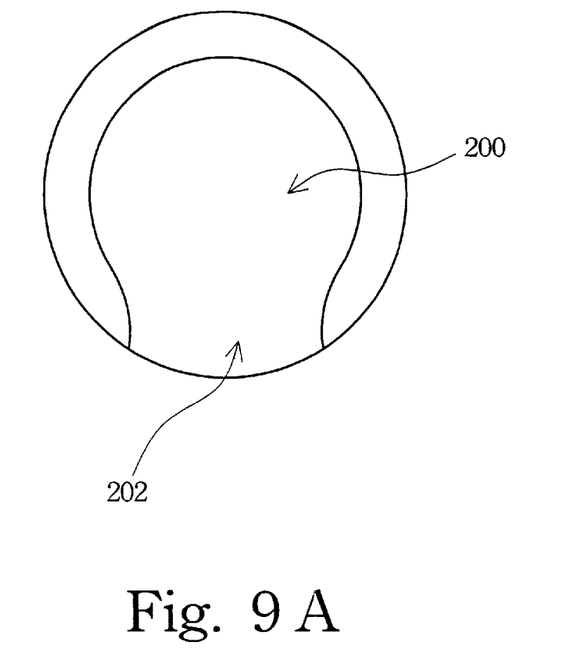
FIG. 9A is a vertical view of the headrest device.
Figure 9B:
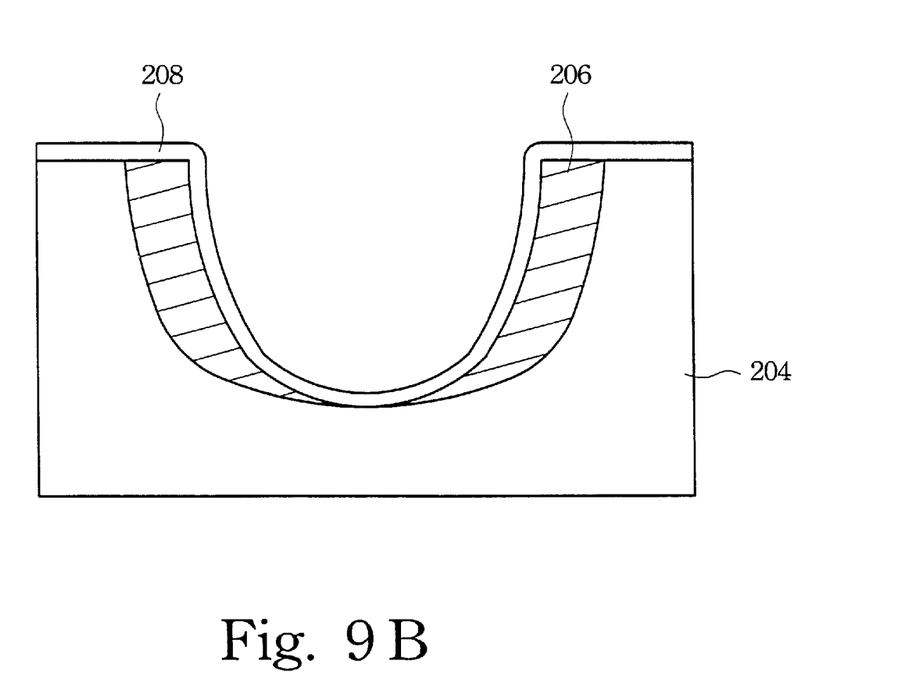
FIG. 9B is a profile view of the headrest device.

FIG. 9A and FIG. 9B show a concave area 200 in the middle most and a neck-holding area 202 of the preformed shape pillow, the invention.

The improved head holder of this invention contains 3 major parts: the base 204, the supplement 206 and the direct contact piece 208. The base 204 is designed according to the ideal skull shape, the size of which can be larger than the actual size of the user's head. The supplement 206 is placed on the base, functioning for the smaller size of the non-compressed preformed shape pillow for the younger or smaller infant, which can be replaced or removed once the baby grows. The direct contact piece 208 is located on the supplement 206, making the baby contact the whole area of the pillow. The design of the shape and marking of the pillow can be varied for aeration, anti-perspiration, and thermolysis. The piece can be placed over any size of supplement or base, reduce the pressure from weight, and fitting the supplement and base well.

In general, the material for the base, supplement or direct contact piece can be silicon rubber, polyurethane, plant fiber, artificial fats, polyethylene, polystyrene, PVC, ABS, gel, polymer, foamed rubber, and plastics materials etc. The invention is not limited in the use of any material above.

Figure 10A:
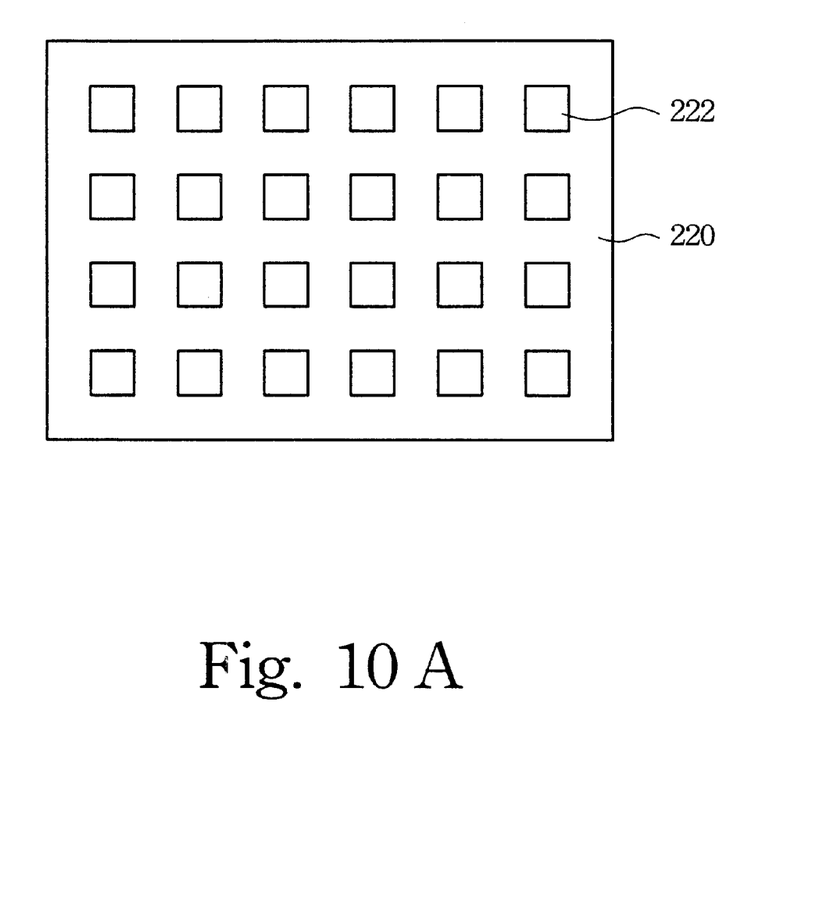
FIG. 10A is a vertical view of a supplement of the headrest device.
Figure 10B:
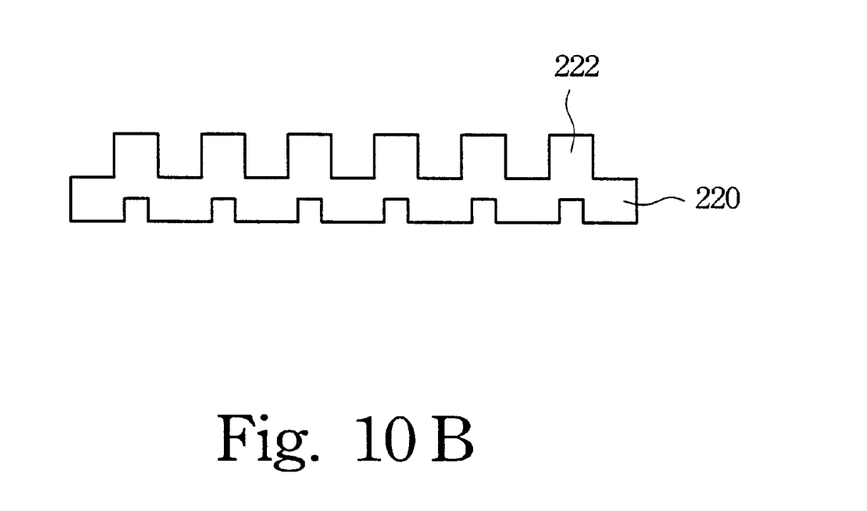
FIG. 10B is a profile view of a supplement of the headrest device.

The diagram of the structure of the direct contact piece 220 is shown in FIG. 10A and FIG. 10B, in which the piece 220 has many symmetric or asymmetric rows of granular objects on the surface adapted to facilitate the passage of air. The piece can be made by any kind of material for the purpose such as cloth and the cloth used in this invention is not limited to any kind. The structure of the piece is adapted for increased passage of air when the baby's head contacts the piece, which can therefore be designed freely for the baby in different sleeping positions and functions like the supplement for fine-tuning.

Figure 11A:
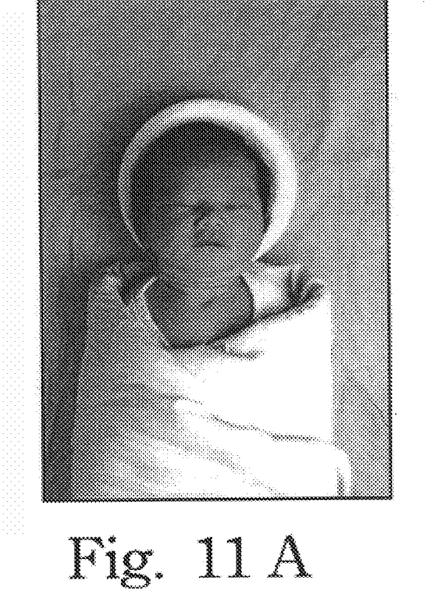
FIG. 11A and FIG. 11B illustrate a practicing instance of a baby who is in use of the device.
Figure 11B:
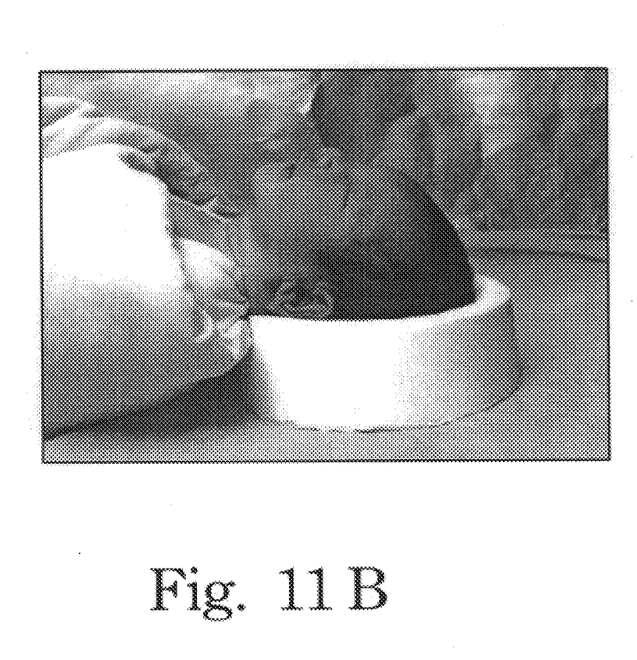
Figure 11C:
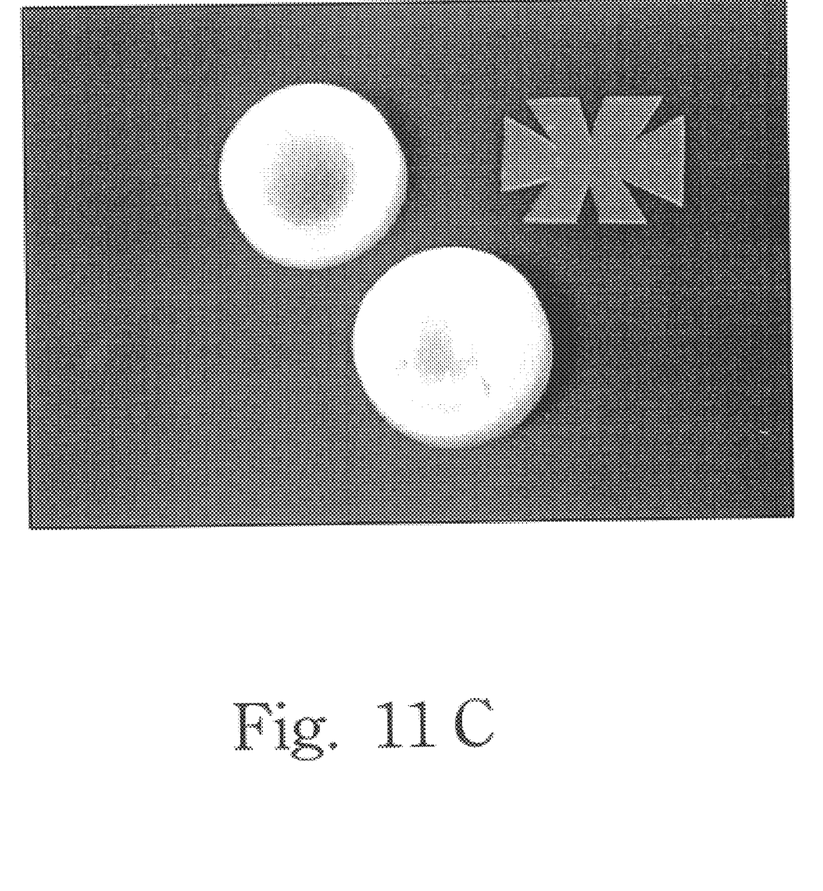
FIG. 11C shows an example of the non-compressed preformed shape headrest and a piece of the supplement.

An additional point to be noted is that the headrest is not confined to include all of the previously described components, i.e. the base 204, the supplement 206 and the direct contact piece 208. The present invention can include either the base with the supplement, the base with the supplement and piece, or the base with the piece. This invention is not limited to any particular combined structure. The instance in the use of this invention to the infant can be viewed in FIG. 11A and FIG. 11B. One example of the present invention is shown in FIG. 11C.

As we have seen above, this invention has many advantages. Firstly, this invention provides a preformed shape headrest for the protection of the skull shape of premature and newborn babies from underlying deformity and to maintain the beauty of the face and skull shape after growth. Secondly, the headrest is designed in accordance with the skull shape of the infant, and thus it can average the pressure from weight and distribute it evenly over the headrest. By use of the headrest device, the baby acquires strong support on his neck and head with comfort. Specifically, the preformed shape headrest is capable of adjusting for torticollis and skull deformity occurring from other reasons. Since this invention make a use of removable supplement 206, the headrest can continuously be used, as the baby grows up to the next stage, by taking away the supplement without any change of the base. For instance, the headrest can be used with the base along with the supplement as the baby's pillow when he weighs around 3,100 g. With his growth up to e.g. 3,800 g, the baby skull is grows bigger as well. To continue to use the headrest, the only thing to do is to draw the supplement away from the base and the headrest will just fit the size of the baby's head.

As is understood by a person skilled in the art, the foregoing preferred embodiments of the present invention are illustrative of the invention rather than limiting of the invention. It is intended to cover various modifications and similar arrangements included within the spirit and scope of the appended claims, the scope of which should be accorded the broadest interpretation so as to encompass all such modifications and similar structures.

What is claimed is:

1. A pediatric headrest device comprising:
   a base having a first concave region and a first depressed segment adjacent the first concave region;
   a supplement attached to the base adjacent the first concave region and the first depressed segment having a second concave region and a second depressed segment; and a contact piece attached to the supplement adjacent the second concave region and the second depressed segment having a third concave region and a third depressed segment having a third concave region and the third depressed region conform to an average contour of a survey of a plurality of infants' skulls and necks respectively.

2. The device of claim 1, wherein the base, supplement, and contact piece have a hardness between 0 and 40 as measured by Shore A hardness.

3. The device of claim 1, wherein a compression ratio of the device is less than 25%, wherein the compression ratio is defined as a decrease of a thickness of the device after the infant's head resting on the device is compared with an original thickness of the device.

4. The device of claim 1, wherein the device is made of material selected from a group consisting of silicone rubber and polymers.

5. The device of claim 1, wherein at least two of the base, the supplement, and the contact piece are made as a unitized assembly.

6. The device of claim 1, wherein the third concave region and third depressed segment have a plurality of contours.

7. The device of claim 6, wherein the plurality of contours of the third concave region and third depressed segment conform to a plurality of average skull shapes of children of a plurality of ages.

8. A method of improving pediatric skull comprising:
   providing a base having a first concave region and a first depressed segment adjacent the first concave region;
   providing a supplement attached to the base adjacent the first concave region and the first depressed segment having a second concave region and a second depressed segment;
   providing a contact piece attached to the supplement adjacent the second concave region and the second depressed segment having a third concave region and a third depressed region wherein the third concave region and the third depressed region conform to an average contour of a survey of a plurality of infants' skulls and necks respectively;
   placing a pediatric patient in a supine position;
   placing the pediatric patient's head on the contact piece; and maintaining the contact piece to track the growth of the pediatric patient.

9. The method of claim 8, wherein the base, supplement, and contact piece have a hardness between 0 and 40 as measured by Shore A hardness.

10. The method of claim 8, wherein the device is made of material selected from a group consisting of silicone rubber and polymers.

11. The method of claim 8, wherein at least two of the base, the supplement, and the contact piece are made as unitized assembly.

12. The method of claim 8, wherein the third concave region and third depressed segment have a plurality of contours.

13. The method of claim 12, wherein the plurality of contours of the third concave region and third depressed segment conform to a plurality of average contours of a plurality of average skull shapes of children of a plurality of ages.

\* \* \* \* \*